US006783533B2

(12) United States Patent
Green et al.

(10) Patent No.: US 6,783,533 B2
(45) Date of Patent: Aug. 31, 2004

(54) ATTACHABLE/DETACHABLE REAMING HEAD FOR SURGICAL REAMER

(75) Inventors: James M. Green, Portland, OR (US); Stanley J. Kmiec, Jr., Coopersburg, PA (US)

(73) Assignee: Sythes AG Chur, Chur (CH)

( * ) Notice: Subject to any disclaimer, the term of this patent is extended or adjusted under 35 U.S.C. 154(b) by 245 days.

(21) Appl. No.: 09/989,169

(22) Filed: Nov. 21, 2001

(65) Prior Publication Data

US 2003/0097133 A1 May 22, 2003

(51) Int. Cl.⁷ .............................................. A61B 17/16
(52) U.S. Cl. ...................................................... 606/80
(58) Field of Search ........................... 606/80, 170, 180

(56) References Cited

U.S. PATENT DOCUMENTS

| | | |
|---|---|---|
| 2,525,329 A | 10/1950 | Wyzenbeek |
| 3,528,425 A | 9/1970 | Banko |
| 3,554,192 A | 1/1971 | Isberner |
| 3,584,629 A | 6/1971 | Hoef et al. |
| 3,732,858 A | 5/1973 | Banko |
| 3,835,858 A | 9/1974 | Hagen |
| 3,976,077 A | 8/1976 | Kerfoot, Jr. |
| 4,362,161 A | 12/1982 | Reimels et al. |
| 4,378,212 A | 3/1983 | Waldron |
| 4,445,509 A | 5/1984 | Auth |
| 4,553,957 A | 11/1985 | Williams et al. |
| 4,573,979 A | 3/1986 | Blake |
| 4,646,738 A | 3/1987 | Trott |
| 4,649,919 A | 3/1987 | Thimsen et al. |
| 4,706,659 A | 11/1987 | Matthews et al. |
| 4,735,604 A | 4/1988 | Watmough et al. |
| 4,751,922 A | 6/1988 | DiPietropolo |
| 4,803,982 A | 2/1989 | Baker |
| 4,811,734 A | 3/1989 | McGurk-Burleson et al. |

(List continued on next page.)

FOREIGN PATENT DOCUMENTS

| | | |
|---|---|---|
| DE | 197 19 051 A1 | 11/1998 |
| EP | 0 440 371 A1 | 8/1991 |
| EP | 0 508 710 A1 | 10/1992 |
| EP | 0 666 059 A2 | 2/1995 |
| EP | 0 836 833 A2 | 4/1998 |
| EP | 0 895 754 A2 | 2/1999 |
| EP | 0 925 760 A2 | 6/1999 |
| EP | 0 965 308 A1 | 12/1999 |
| JP | 5-103790 | 4/1993 |
| JP | 9-108230 | 4/1997 |
| JP | 10-043193 | 2/1998 |
| JP | 10-118084 | 5/1998 |
| JP | 10-216138 A | 8/1998 |
| JP | 10-295696 | 11/1998 |
| JP | 11-089849 | 4/1999 |
| JP | 11-226031 | 8/1999 |
| JP | 11-262499 | 9/1999 |
| WO | WO96/31307 | 10/1996 |
| WO | WO97/03617 | 2/1997 |
| WO | WO97/24991 | 7/1997 |
| WO | WO98/42263 | 10/1998 |
| WO | WO99/47051 | 9/1999 |
| WO | WO00/44291 | 8/2000 |

*Primary Examiner*—Eduardo C. Robert
(74) *Attorney, Agent, or Firm*—Jones Day

(57) ABSTRACT

A device for expedited reaming of a medullary canal having a detachable reaming head is disclosed. The device includes a reamer head connected at the distal end of a rotatable drive shaft. The reamer head has a cutting head with a plurality of blades and flutes therebetween at a first end and a plurality of resilient arms at a second end. The device may also includes an aspiration tube which fits over the rotatable drive shaft and a reamer head retainer which rotatably engages the reamer head. In addition, the reamer head may be detached from the reamer device for future re-use by using a reamer head removing device.

18 Claims, 19 Drawing Sheets

U.S. PATENT DOCUMENTS

| | | |
|---|---|---|
| 4,830,000 A | 5/1989 | Shutt |
| 4,842,578 A | 6/1989 | Johnson et al. |
| 4,844,064 A | 7/1989 | Thimsen et al. |
| 4,867,157 A | 9/1989 | McGurk-Burleson et al. |
| 4,904,238 A | 2/1990 | Williams |
| 5,007,911 A | 4/1991 | Baker |
| 5,007,917 A | 4/1991 | Evans |
| 5,019,036 A | 5/1991 | Stahl |
| 5,074,841 A | 12/1991 | Ademovic et al. |
| 5,112,299 A | 5/1992 | Pascaloff |
| 5,114,399 A | 5/1992 | Kovalcheck |
| 5,122,134 A | 6/1992 | Borzone et al. |
| 5,190,548 A | 3/1993 | Davis |
| 5,217,479 A | 6/1993 | Shuler |
| 5,222,956 A | 6/1993 | Waldron |
| 5,224,929 A | 7/1993 | Remiszewski |
| 5,236,433 A | 8/1993 | Salyer |
| 5,269,785 A | 12/1993 | Bonutti |
| 5,312,408 A | 5/1994 | Brown |
| 5,330,480 A | 7/1994 | Meloul et al. |
| 5,341,816 A | 8/1994 | Allen |
| 5,380,333 A | 1/1995 | Meloul et al. |
| 5,403,317 A | 4/1995 | Bonutti |
| 5,405,348 A | 4/1995 | Anspach, Jr. et al. |
| 5,443,468 A | 8/1995 | Johnson |
| 5,487,747 A | 1/1996 | Stagmann et al. |
| 5,489,291 A | 2/1996 | Wiley |
| 5,499,984 A | 3/1996 | Steiner et al. |
| 5,529,580 A | 6/1996 | Kusunoki et al. |
| 5,549,613 A | 8/1996 | Goble et al. |
| 5,569,254 A | 10/1996 | Carlson et al. |
| 5,577,517 A | 11/1996 | Bonutti |
| 5,601,560 A | 2/1997 | Del Rio et al. |
| 5,609,573 A | 3/1997 | Sandock |
| 5,618,293 A | 4/1997 | Sample et al. |
| 5,630,818 A | 5/1997 | Del Rio et al. |
| 5,645,545 A | 7/1997 | Bryant |
| 5,658,290 A | 8/1997 | Lechot |
| 5,685,673 A | 11/1997 | Jarvis |
| 5,690,634 A | 11/1997 | Muller et al. |
| 5,693,047 A | 12/1997 | Meyers et al. |
| 5,693,062 A | 12/1997 | Stegmann et al. |
| 5,694,951 A | 12/1997 | Bonutti |
| 5,720,749 A | 2/1998 | Rupp |
| 5,741,263 A | 4/1998 | Umber et al. |
| 5,759,185 A | 6/1998 | Grinberg |
| 5,792,167 A | 8/1998 | Kablik et al. |
| 5,817,096 A | 10/1998 | Salyer |
| 5,833,628 A | 11/1998 | Yuan et al. |
| 5,893,851 A | 4/1999 | Umber et al. |
| 5,904,687 A | 5/1999 | Del Rio et al. |
| 5,913,859 A | 6/1999 | Shapira |
| 5,913,866 A | 6/1999 | Ginn et al. |
| 5,913,867 A | 6/1999 | Dion |
| 5,916,231 A | 6/1999 | Bays |
| 5,922,003 A | 7/1999 | Anctil et al. |
| 5,928,241 A | 7/1999 | Menut et al. |
| 5,935,131 A | 8/1999 | Bonutti |
| 5,941,891 A | 8/1999 | Walen |
| 5,947,972 A | 9/1999 | Gage et al. |
| 5,951,561 A | 9/1999 | Pepper et al. |
| 5,968,048 A | 10/1999 | Harder |
| 5,971,988 A | 10/1999 | Reccius et al. |
| 5,980,170 A | 11/1999 | Salyer |
| 5,980,525 A | 11/1999 | Bryant et al. |
| 5,993,453 A | 11/1999 | Bullara et al. |
| 6,001,112 A | 12/1999 | Taylor |
| 6,015,411 A | 1/2000 | Ohkoshi et al. |
| 6,042,593 A | 3/2000 | Storz et al. |
| 6,053,923 A | 4/2000 | Veca et al. |
| 6,056,923 A | 5/2000 | Diamond et al. |
| 6,110,176 A | 8/2000 | Shapira |
| 6,132,448 A | 10/2000 | Perez et al. |
| 6,168,599 B1 | 1/2001 | Frieze et al. |
| 6,168,600 B1 | 1/2001 | Grace et al. |
| 6,200,319 B1 | 3/2001 | Storer et al. |
| 6,221,076 B1 | 4/2001 | Albrektsson et al. |
| 6,238,398 B1 | 5/2001 | Lechot |
| 6,245,074 B1 | 6/2001 | Allard et al. |
| 6,258,093 B1 | 7/2001 | Edwards et al. |
| 6,277,121 B1 | 8/2001 | Burkinshaw et al. |
| 6,283,970 B1 | 9/2001 | Lubinus |
| 6,283,971 B1 | 9/2001 | Temeles |
| 6,309,396 B1 | 10/2001 | Ritland |
| 6,325,806 B1 | 12/2001 | Fox |
| 6,332,886 B1 * | 12/2001 | Green et al. .................. 606/80 |
| 6,358,251 B1 | 3/2002 | Mirza |
| 6,383,188 B2 | 5/2002 | Kuslich et al. |
| 6,416,517 B2 | 7/2002 | Harder et al. |
| 6,447,518 B1 | 9/2002 | Krause et al. |
| 6,451,023 B1 | 9/2002 | Salazar et al. |
| 6,451,036 B1 | 9/2002 | Heitzmann et al. |
| 6,468,227 B2 | 10/2002 | Zimmon |
| 6,468,289 B1 | 10/2002 | Bonutti |
| 6,475,221 B1 | 11/2002 | White et al. |
| 6,517,581 B2 | 2/2003 | Blamey |
| RE38,018 E | 3/2003 | Anctil et al. |
| 6,543,455 B2 | 4/2003 | Bonutti |
| 6,592,531 B2 | 7/2003 | Bonutti |
| 2002/0007190 A1 | 1/2002 | Wulfman et al. |
| 2002/0029055 A1 | 3/2002 | Bonutti |
| 2002/0045903 A1 | 4/2002 | Bonutti |
| 2002/0055755 A1 | 5/2002 | Bonutti |
| 2002/0082631 A1 | 6/2002 | Bonutti |
| 2002/0091403 A1 | 7/2002 | Bonutti |
| 2002/0099401 A1 | 7/2002 | Bonutti |
| 2002/0151902 A1 | 10/2002 | Reidel et al. |
| 2002/0188299 A1 | 12/2002 | Reiley et al. |
| 2003/0009147 A1 | 1/2003 | Bonutti |
| 2003/0009172 A1 | 1/2003 | Bonutti |
| 2003/0163136 A1 | 8/2003 | Joist |

* cited by examiner

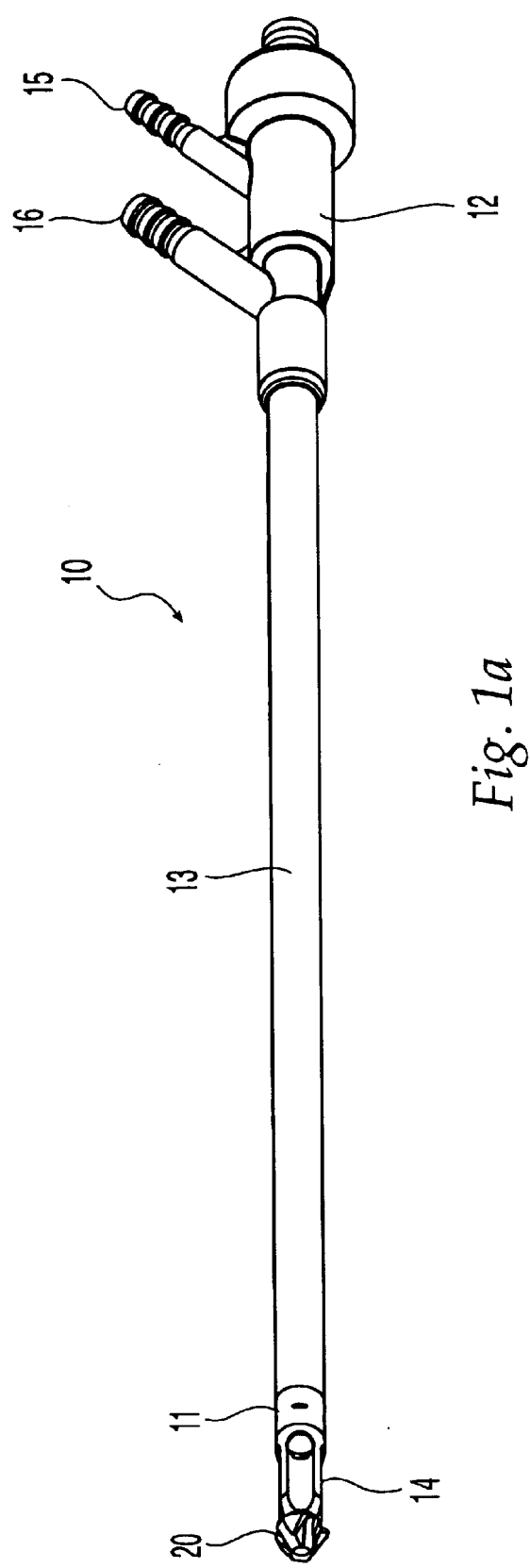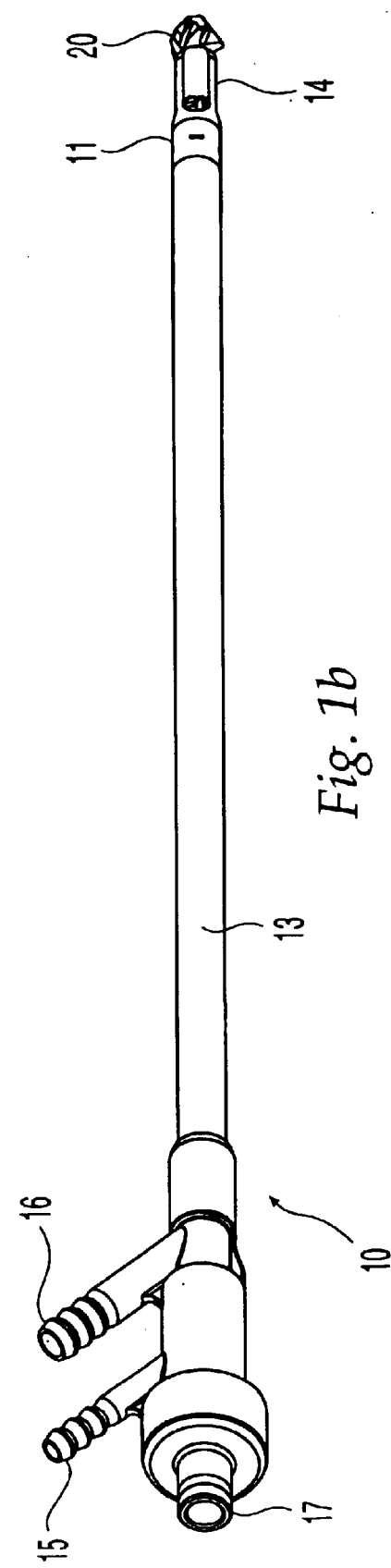
Fig. 1a
Fig. 1b

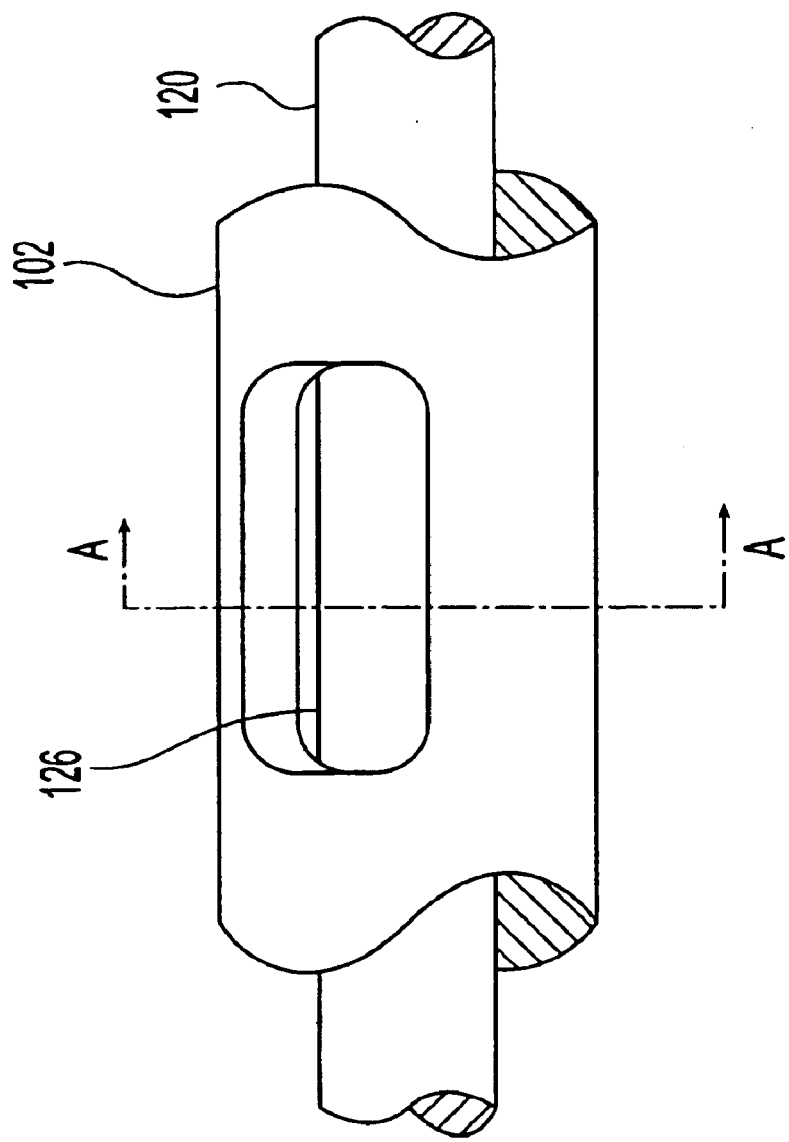
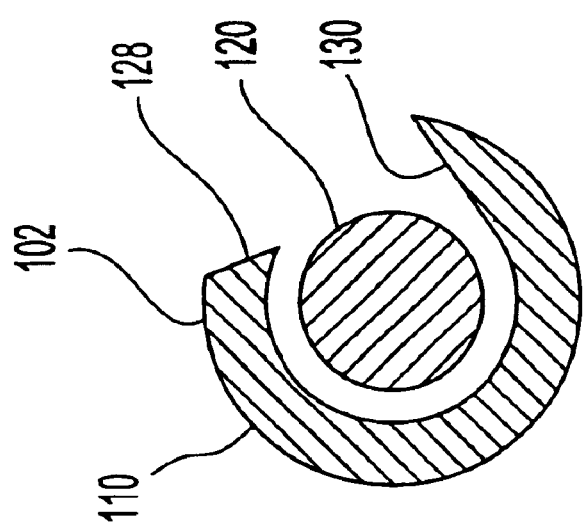
Fig. 11
Fig. 12

ATTACHABLE/DETACHABLE REAMING HEAD FOR SURGICAL REAMER

FIELD OF THE INVENTION

The present invention is directed to a device for bone tissue removal, and in particular to a device having a detachable head for expedited reaming of a medullary canal.

BACKGROUND OF THE INVENTION

A wide variety of devices for cutting and removing bone tissue are known in the art. In general, these devices utilize a rotating cutting tip, similar to a drill, located at a distal end of a drive shaft. Bone cutting devices for use in reaming the medullary canal typically use a flexible drive shaft because the medullary canals of bones are seldom straight and usually will have some degree of curvature. Most reamers also have a central bore through both the reamer and the drive shaft. The central bore is intended to receive a long, small diameter guide pin or wire which is initially inserted into the medullary canal to act as a track for the advancing reamer.

Reamers are used in orthopedic surgery to prepare the medullary canals of bone for a wide variety of surgical procedures including total hip and knee replacement, nail insertion for stabilization of a long bone fracture, intramedullary osteotomy, and bone harvesting for grafting purposes.

From both a mechanical and a biological point of view, medullary reaming is particularly beneficial in improving the performance of implants. Specifically, reaming expands the medullary canal so that larger diameter implants can be inserted. These larger diameter implants are less likely to fail. In fact, certain fractures require over-reaming so that larger implants can be used. Without reaming, the surgeon must use a "best guess" estimate when selecting the diameter of the implant. The medical literature contains numerous case studies reporting the adverse consequences of an inaccurate estimate. Reaming provides a direct measurement of the diameter of the medullary canal, and thereby allows for the selection of an implant that precisely fills the canal. As a result, the stability of the fracture site is enhanced by achieving endosteal contact. When implants do not fill the medullary canal, load sharing between the implant and the bone is decreased. This increases the load that is transferred to the implant and promotes both implant failure and stress shielding of the bone.

Despite such benefits, negative consequences have also been associated with medullary reaming. In particular, current procedures for reaming the medullary cavity can result in an increase in both temperature and pressure. Like most any process in which material is being removed, reaming causes generation of heat. Furthermore, a hydraulic pressure, which far exceeds that of blood pressure, builds up in the cavity during reaming. The reamer acts as a hydraulic piston within the bone cavity, and if the contents of the canal, which include a mixture of medullary fat, blood, blood clots, and bone debris, enter the blood stream, an embolism can result. Excessive heat has been associated with an increased incidence of aseptic necrosis of the cortex and elevated pressure has been associated with an increased risk of fat emboli. These complications are more likely to occur in patients when extenuating factors such as shock, existing lung contusion, multiple traumas, or pre-existing pulmonary impairment are present. In these situations, the preferred method of reaming would usually not be performed due to the increased risks involved.

Various devices and methods exist for reducing the intramedullary pressure build-up during reaming. For example, in prosthetic joint replacement, a distal venting hole, a large insertion hole, and a modified technique for cement insertion have all been shown to have some success in reducing pressure, and presumably, the chance of fat embolism. Venting holes in the bone only have little effect because their diameter is typically too small and local peak values must be assumed during the passage of the reamer. Similarly, reaming the medullary cavity less does not prevent pressure increase. In fact, pressure can be high even for reamers of small diameter.

Another technique which has been used in an attempt to reduce temperature and pressure is to perform the reaming in multiple steps with increasing size of reamers with each step. As a result, reaming procedures are done slowly with the application of gentle pressure and requiring multiple passes. Usually reaming is performed in 1 mm diameter increments until the bone cortex is reached and then in 0.5 mm increments thereafter. In this regard, the reaming is carried out with less compression force and the intramedullary pressure can be easily reduced with most reaming devices utilizing this slow process. A faster reaming process utilizing fewer passes would be desirable in order to reduce operating time and medical costs.

The reaming device disclosed in U.S. patent application Ser. No. 09/495,932 entitled "Surgical Reamer and Method of Using Same" filed on Feb. 2, 2000, the entire contents of which is expressly incorporated herein by reference, allows reaming of a medullary canal at an enhanced rate without the negative consequences associated with medullary reaming such as increasing the risk of fat emboli and heat necrosis upon cutting and removal of bone tissue. Furthermore, the reaming device can be single use so after the surgical procedure is completed, the flexible aspiration tube along with the fixed reamer head can be discarded.

By having a single use reaming device, the problems associated with the reamer head becoming blunt over time are avoided. For example, the problems of greater intramedullary pressures and greater increases in cortical temperature resulting from the continued use of a blunted reamer are avoided. In addition, by having a single use reaming device, the careful attention of surgeons and operating staff to treat the reamers gently is not necessary.

However, there are some drawbacks to having a single use reaming device with a fixed reamer head. Typically, the anatomy of patients will vary requiring different reamers and reamer heads to accommodate the variance in the patient anatomy. For example, some patients will have larger long bones which may require larger reamer heads. Since the reamer head is fixed to the rest of the reaming device, the surgeons and operating staff would have to maintain a full inventory of different reamers to accommodate the different patient anatomies. Maintaining a full inventory of reamers would require a lot of space and would be costly. As a result, a single use reaming device with a detachable reamer head is desirable to avoid the problems of having to maintain a full inventory of reamers. By having a detachable reaming head, the surgeon and operating staff would have to maintain only a few reaming devices with a full inventory of reaming heads. This would require less space and would be less costly.

In addition, reamer heads generally are durable and a few uses will not impair the reliability or efficacy of the reamer head. Accordingly, having a detachable reaming head allows for future re-use of the reamer head thereby reducing the cost associated with the reaming procedure.

Thus, there exists a need for a device for reaming a medullary canal at an enhanced rate without increasing the risk of fat emboli and heat necrosis upon cutting and removal of bone tissue and which allows the reamer head to be detached for future re-use.

SUMMARY OF THE INVENTION

The present invention relates to a device for reaming a medullary canal of a bone. The device includes a rotatable drive shaft connected at the proximal end to a rotational drive element and a detachable reamer head rotatably coupled to the distal end of the drive shaft. The reamer head has a tubular shank with resilient arms coupling to the distal end of the drive shaft and a cutting head integral with the shank and having a plurality of blades. Flutes are located between adjacent blades.

The drive shaft and reamer head each may have a cannulation. These two cannulations are aligned when the tubular shank and the resilient arms are engaged with the drive shaft to form a center channel. One use for this channel is for receiving a guide wire that can be used to direct the device in the medullary canal.

The device may also include an aspiration tube for removing cut material generated by the reamer head. The aspiration tube has a manifold assembly at a proximal end and a lumen configured and dimensioned to receive the drive shaft. The aspiration tube also is connected to a reamer head retainer via a retaining ring at a distal end. Preferably, the center channel is in fluid communication with an irrigation source to provide irrigation to the cutting head. The manifold assembly may include an irrigation port connected to the irrigation source and an irrigation chamber in fluid communication with the irrigation port. The irrigation fluid travels from the irrigation chamber through an opening on the drive shaft and into the center channel.

The reamer head retainer rotatably engages the reamer head via an internal shoulder and the reamer head resilient arms. The reamer head retainer further has a plurality of ports which are in fluid communication with the flutes of the reamer head and the distal end of the lumen of the aspiration tube. The proximal end of the lumen of the aspiration tube is in fluid communication with a suction source. Preferably, the manifold assembly includes an aspiration port connected to the suction source to assist in the removal of the cut material.

The invention also relates to removing the reamer head from the reamer head retainer for future re-use by using a reamer head removing device. The reamer head removing device engages the resilient arms of the reamer head disengaging the resilient arms from the reamer head retainer thereby allowing the reamer head to be detached from the reamer head retainer.

BRIEF DESCRIPTION OF THE DRAWINGS

Preferred features of the present invention are disclosed in the accompanying drawings, wherein similar reference characters denote similar elements throughout the several views, and wherein:

FIG. 1A is a perspective view from the distal left side of one embodiment of a reamer device according to the present invention;

FIG. 1B is a perspective view from the proximal right side of the device of FIG. 1A;

FIG. 11 is a perspective view of a portion of the drive shaft assembly of FIG. 4 with a guide wire inserted in the cannulation of the drive shaft;

FIG. 12 is a cross-sectional view of the drive shaft assembly taken along line A—A of FIG. 11;

DETAILED DESCRIPTION OF THE PREFERRED EMBODIMENTS

Figure 2:
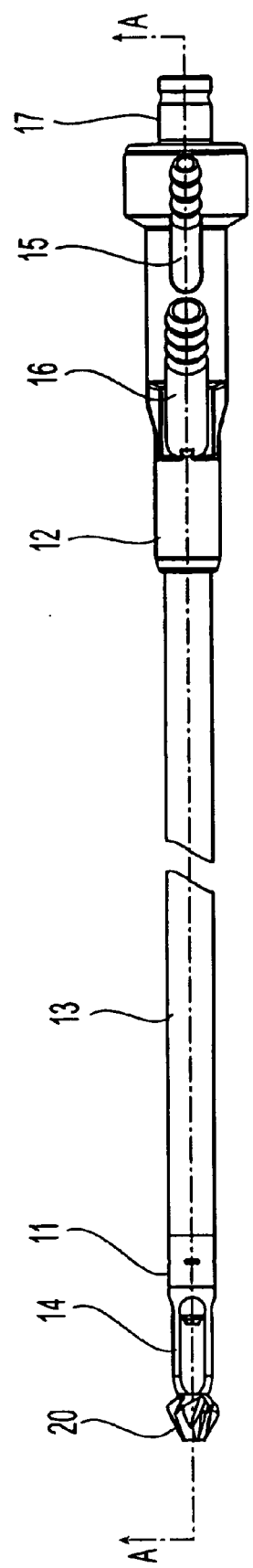
FIG. 2 is a top view of the reamer device of FIGS. 1A and 1B.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Figure 3:
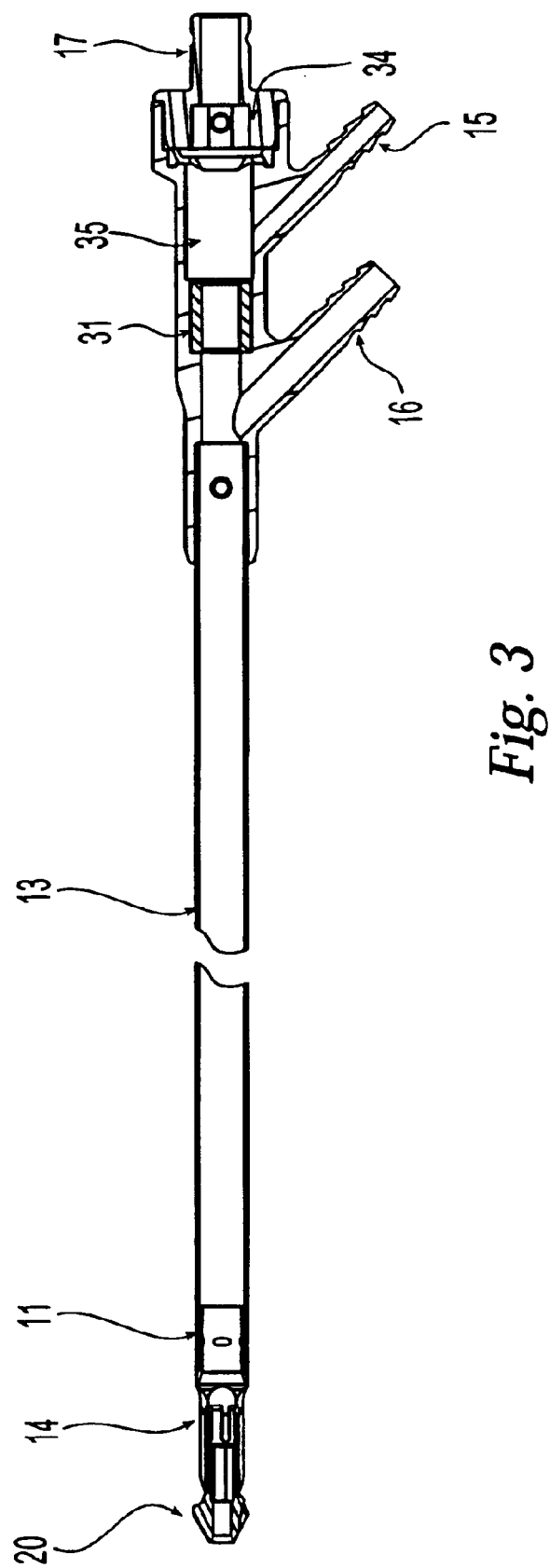
FIG. 3 is a cross-sectional view of the device taken along line A—A of FIG. 2.

Referring to FIGS. 1–3, a preferred embodiment of a reamer 10 according to the present invention comprises a reamer head 20 located at a distal end of reamer 10 for reaming a medullary canal, a flexible aspiration tube 13 for suction and removal of the emulsified bone and other material generated by reamer head 20, a reamer head retainer 14 and retaining ring 11 for retaining reamer head 20 on aspiration tube 13 while still allowing rotation of reamer head 20 with respect to aspiration tube 13 and retainer head retainer 14, and a manifold assembly 12 at a proximal end of reamer 10. Thus, as used in this application, the term distal designates the end or direction near reamer head 20 and toward the front of reamer 10, and the term proximal designates the end or direction near manifold assembly 12 and toward the rear of reamer 10. The term longitudinal designates an axis central to aspiration tube 13.

Aspiration tube 13 is flexible so that it can bend to accommodate curvature of the bone and is preferably made of a translucent material so that the aspirated material can be observed. Manifold assembly 12 has an irrigation port 15 and an aspiration port 16 for connecting to an irrigation source and aspiration means respectively. A drive shaft coupling 17 is located at the proximal end of manifold assembly 12. Drive shaft coupling 17 can be readily attached and detached to a drive shaft or some other means for rotating reamer head 20.

Figure 4:
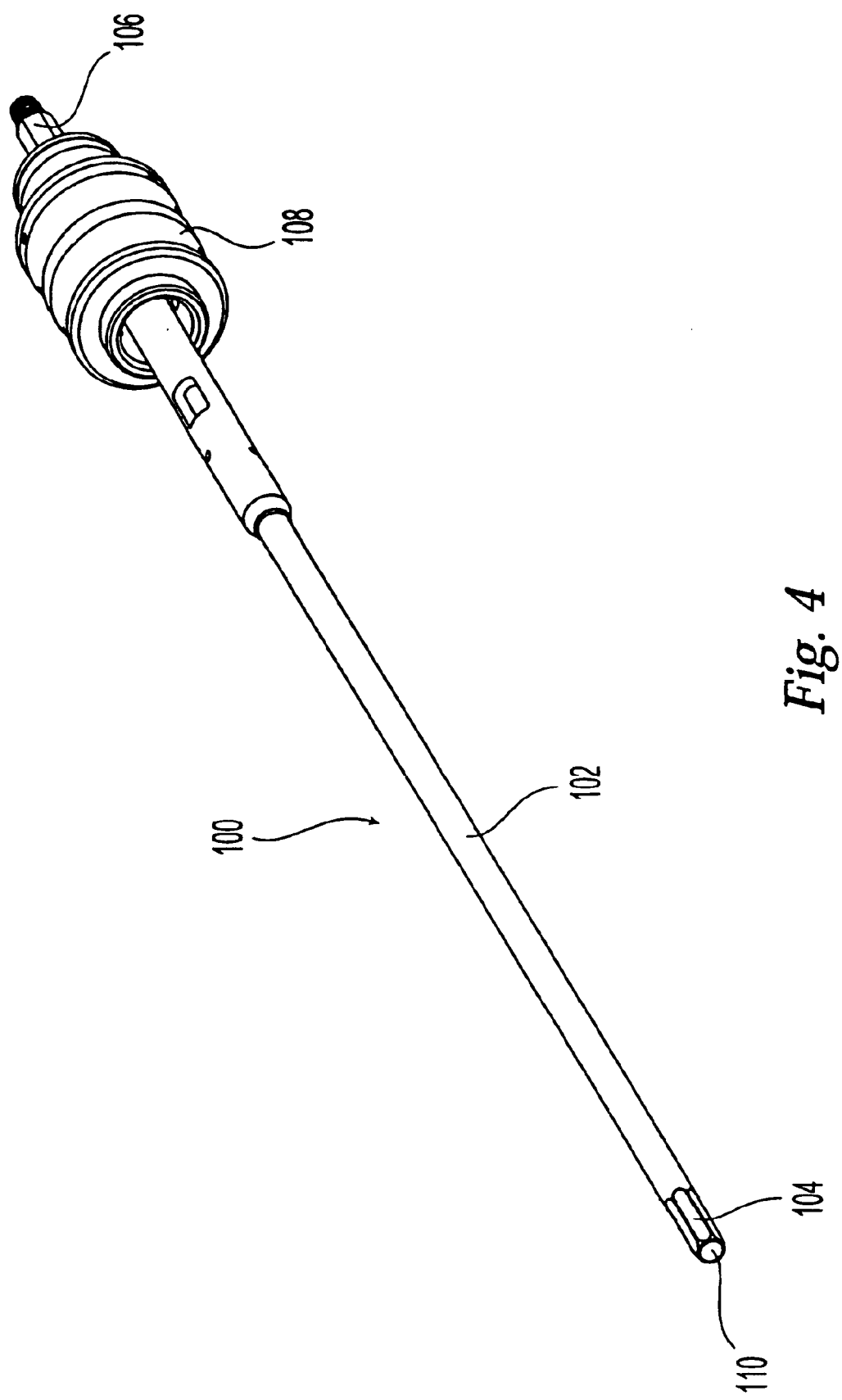
FIG. 4 is a perspective view of one embodiment of a drive shaft assembly according to the present invention.
Figure 5:
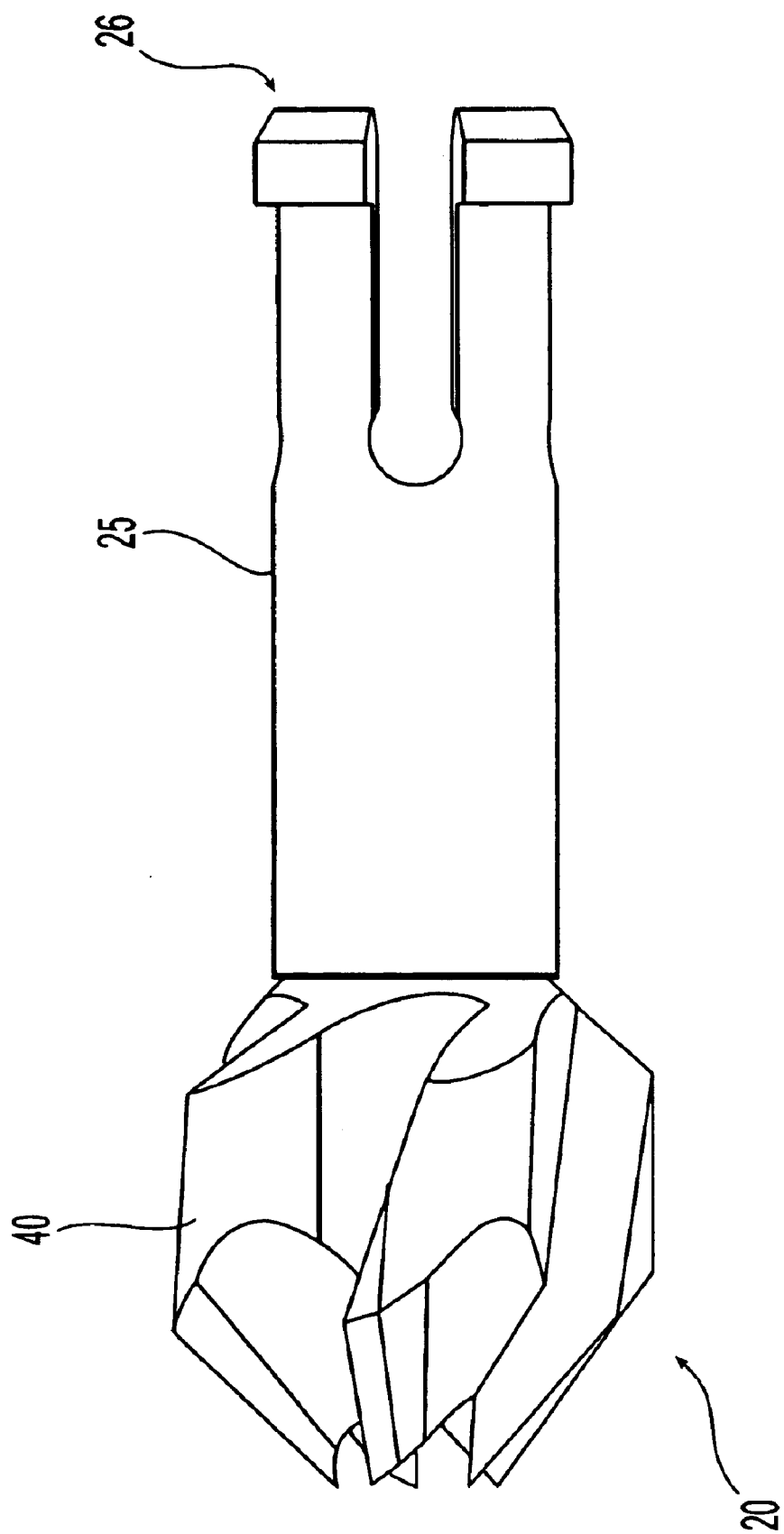
FIG. 5 is a side view of one embodiment of a reamer head according to the present invention.

FIG. 4 shows a drive shaft assembly 100 that can be used with reamer 10 to rotate reamer head 20 at sufficient speeds to ream the medullary canal. The use of a drive shaft assembly 100 with reamer 10 (or any modular system in which the driving means is contained in a unit that is independent from the reamer) allows drive shaft assembly 100 to be reused with many different reamers. Such modularity is advantageous because different patients and clinical conditions will require different sized reamer heads. Furthermore, reamer 10 can be a single-use, disposable item and drive shaft assembly 100 can be used for an extended period.

Drive shaft assembly 100 includes a flexible drive shaft 102 having a reamer head connector 104 on the distal end for releasably engaging reamer head 20 so that reamer head 20 rotates when flexible drive shaft 102 rotates, a power source connector 106 for connection to a source of power to initiate the rotation of drive shaft 102, and a manifold coupling 108 located between reamer head and power source connector 106 for engaging drive shaft coupling 17. Drive shaft 102 is sized to fit within the lumen of aspiration tube 13. However, as will be described in more detail later, there is sufficient space between the outer wall of drive shaft 102 and the inner wall of aspiration tube 13 to allow transport of aspirated material from reamer head 20 through aspiration tube 13 to aspiration port 16. As was the case for aspiration tube 13, drive shaft 102 is flexible to conform to any curvature of the bone being reamed. Drive shaft 102 has a cannulation 110 for accommodating a guide wire 120.

Figure 14:
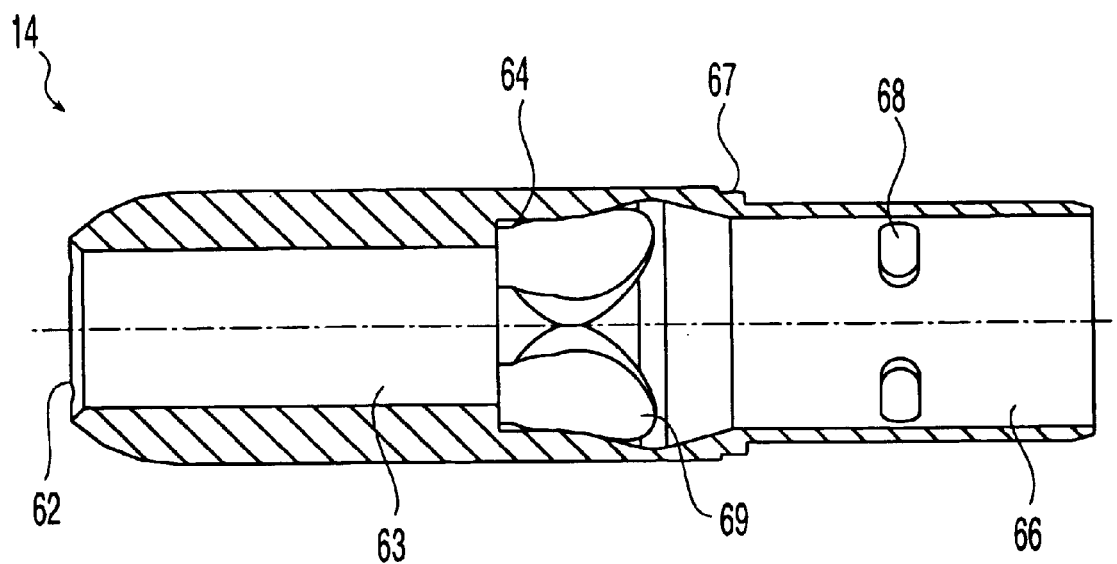
FIG. 14 is a cross-sectional view of an embodiment of the reamer head retainer according to the present invention.

As seen best in FIGS. 11, and 12, there is sufficient space between the outer wall of guide wire 120 and the inner wall of cannulation 110 to allow transport of an irrigation fluid from irrigation port 15 through cannulation 110 to reamer head 20. Drive shaft 102 has an opening 126 that extends from the outer surface of drive shaft 102 to cannulation 110. Opening 126 is positioned on drive shaft 102 so that when drive shaft assembly 100 is coupled to reamer device 10, opening 126 is in fluid communication with irrigation port 15 to allow irrigation to flow through cannulation 110. Opening 126 has curved walls 128, 130. Curved wall 128 bows out to have a convex profile and curved wall 130 curves inward to have a concave profile. The curvature of curved walls 128, 130 helps to draw water into cannulation 110 as drive shaft 102 rotates (which with respect to FIG. 14 is in the counterclockwise direction).

Any suitable means for releasably joining manifold coupling 108 and drive shaft coupling 17 can be used. Preferably, a quick connect mechanism is used for rapid coupling and uncoupling. For example, manifold coupling 108 can have a spring loaded latch mechanism, such as ball bearings, which engage a groove in drive shaft coupling 17. Similarly, any suitable power source and means for securing drive shaft assembly 100 to the power source can be used. As pneumatic tools are widely used in orthopaedic surgery, the power source is preferably an air drive such as the Compact Air Drive available from Synthes (U.S.A.) of Paoli, Pa.

Referring back to FIG. 3, housed within manifold assembly 12 is a sealing element 34 and a sleeve bearing 31. Sealing means 34 and sleeve bearing 31 define an irrigation chamber 35 and provide a hermetic seal to prevent irrigation fluid from escaping irrigation chamber 35 into aspiration port 16 or out the proximal end of reamer device 10 during operation. In addition, sleeve bearing 31 prevents the aspirated emulsified material from entering irrigation chamber 35.

Figure 6:
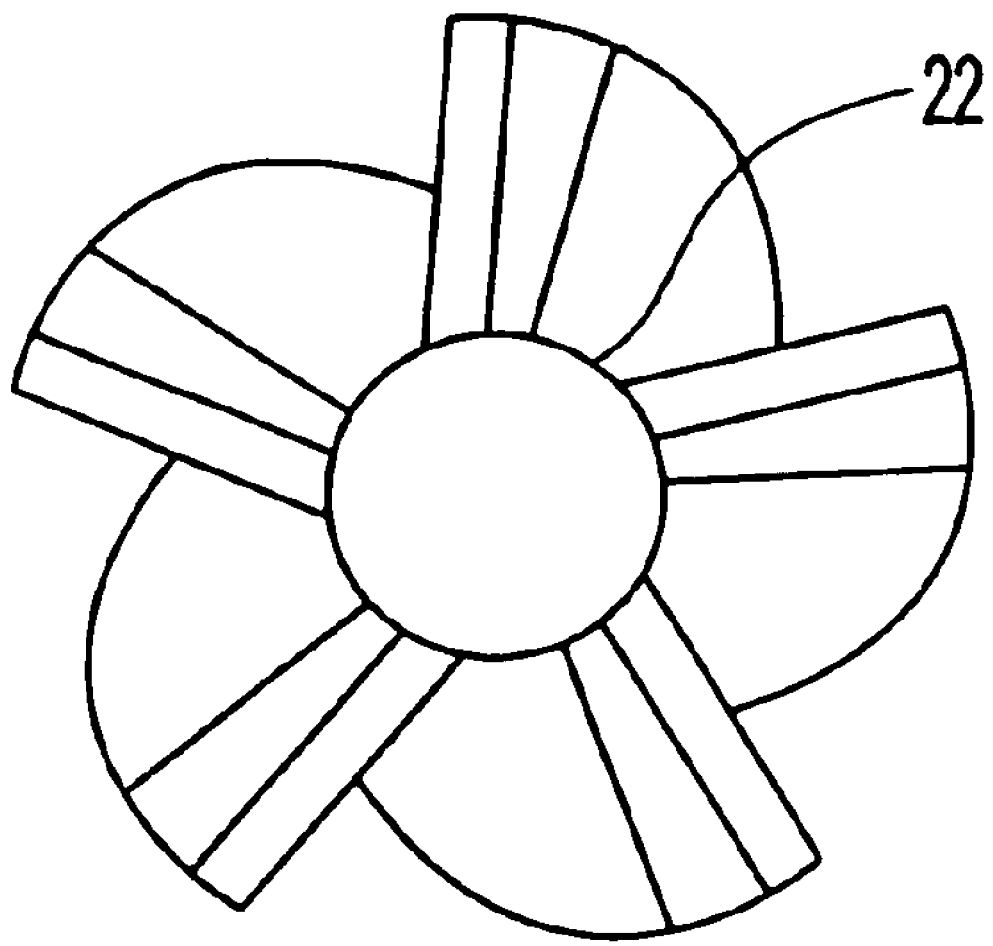
FIG. 6 is a front view of the reamer head of FIG. 5.
Figure 7:
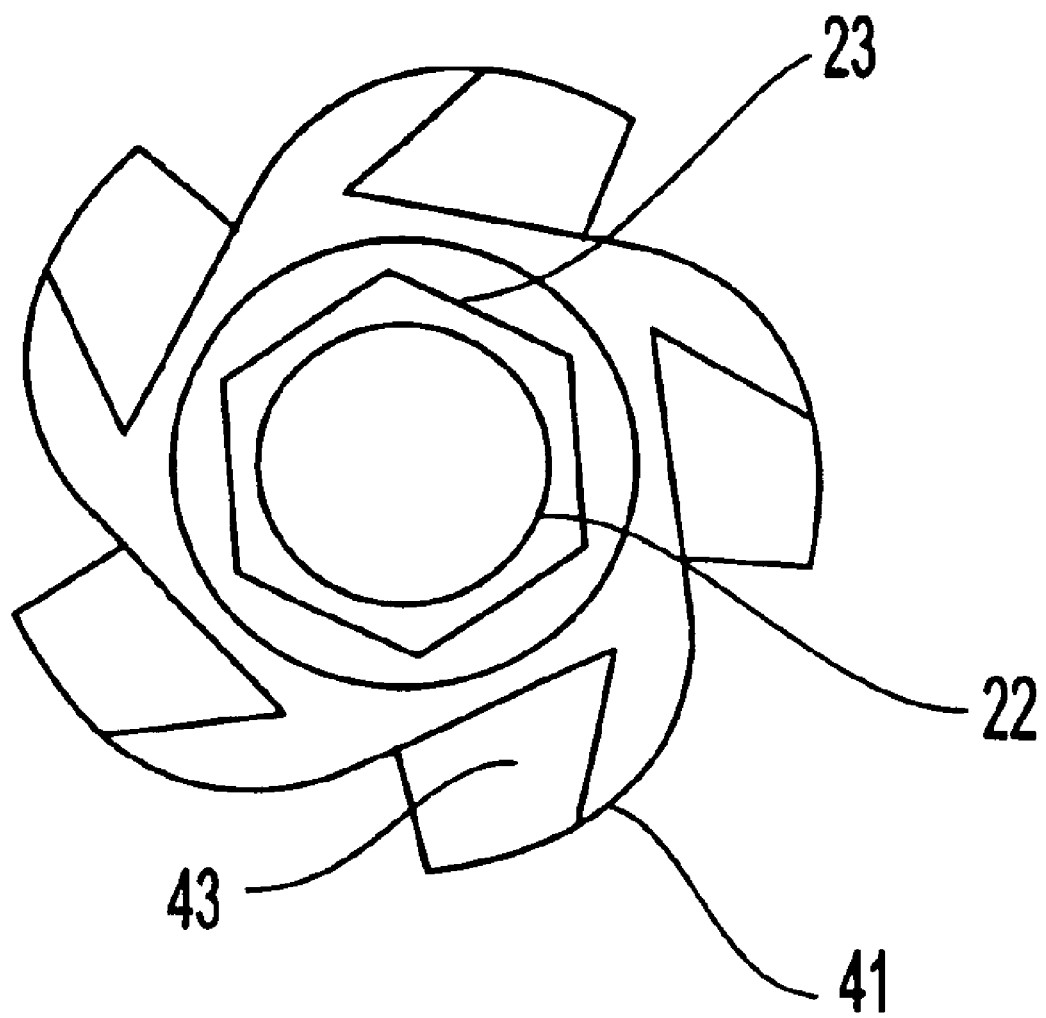
FIG. 7 is a rear view of the reamer head of FIG. 5.
Figure 8:
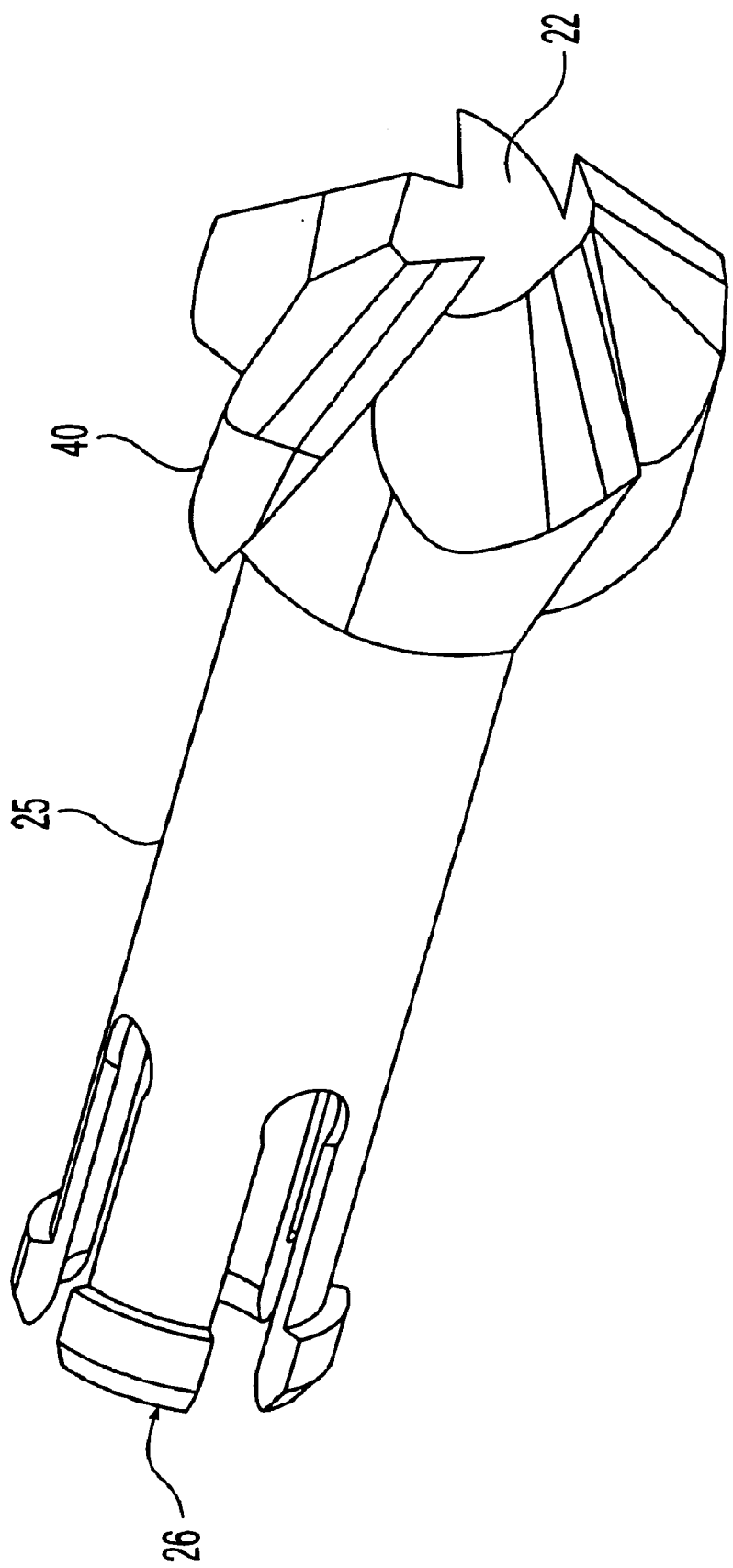
FIG. 8 is a front perspective view of the reamer head of FIG. 5.

Reamer head 20 is preferably made of a stainless steel, although any metallic, polymeric, ceramic, or composite material suitable for cutting bone can be used. A reamer cannulation 22 extends from the distal tip to the proximal end of reamer head 20 (FIGS. 6, 7 and 8). Reamer cannulation 22 is aligned with cannulation 110 of drive shaft 102 so that a guide wire can extend from the proximal end of drive shaft 102 through the distal end of reamer head 20.

Figure 9:
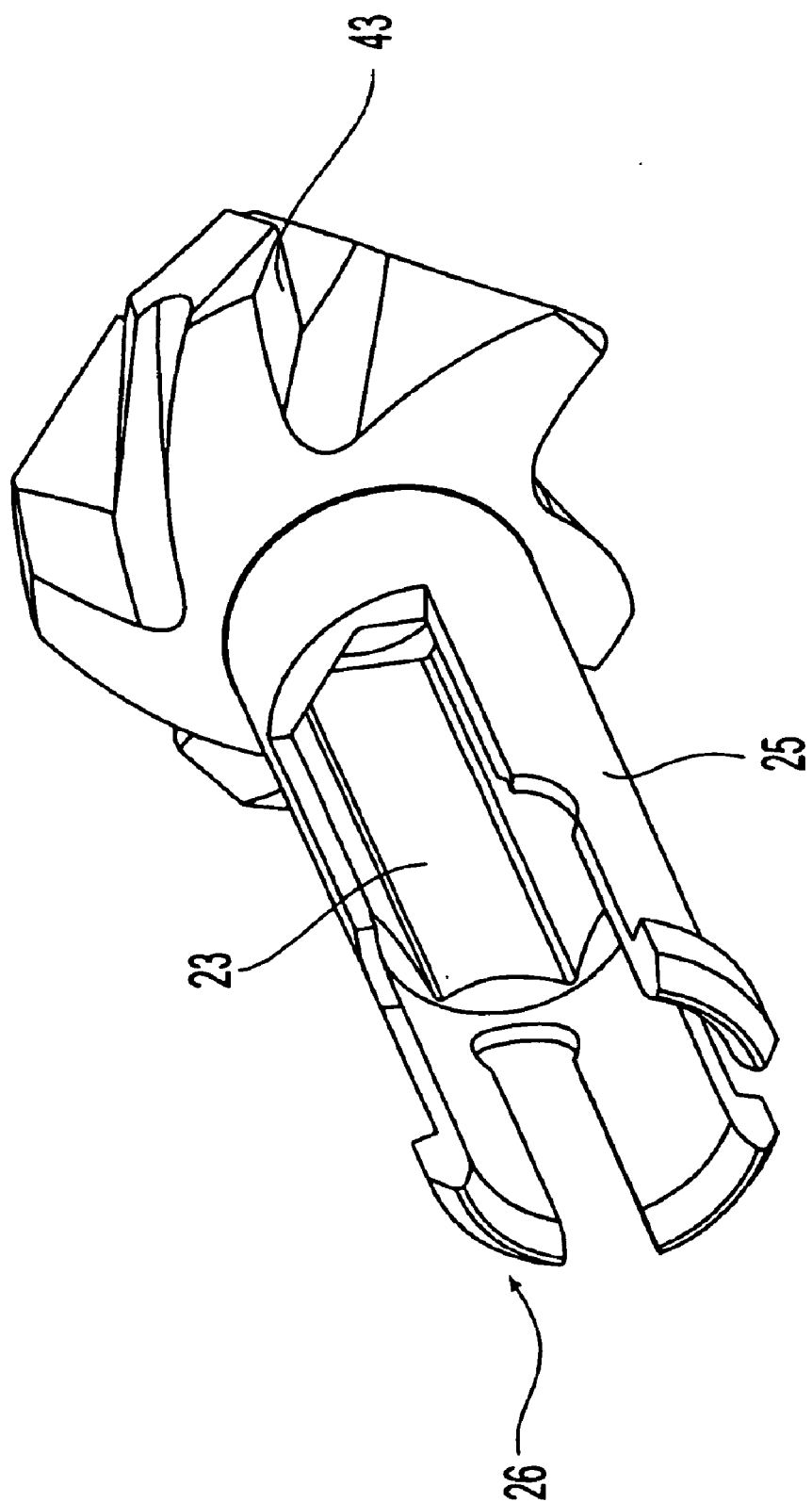
FIG. 9 is a rear perspective view of the reamer head of FIG. 5.

Although many different reamer heads can be used with reamer 10, one embodiment is shown in FIGS. 5–10. As shown in these figures, reamer head 20 consists of a cutting head 40 integral with a tubular shank 25. The periphery of tubular shank 25 is cylindrical and has a plurality of resilient retaining arms 26 located at the proximal end of reamer head 20 which resiliently engage a shoulder on the inside of reamer head retainer 14 permitting reamer head 20 to rotate while maintaining a fixed location longitudinally at the distal end of the aspiration tube 13. As can be seen in FIG. 9, tubular shank 25 has a drive shaft receptor 23 at the proximal end which is configured to accommodate reamer head connector 104 of drive shaft 102 so that reamer head 20 must rotate when drive shaft 102 rotates. Although drive shaft receptor 23 can be of any shape conforming to the exterior profile of reamer head connector 104, it is preferably a female hex feature.

Cutting head 40 of reamer head 20 has a plurality of blades 41, preferably at least five in number, extending radially outwardly from reamer cannulation 22 to form a substantially helical pattern. Correlating the number of blades to the particular blade geometry and rotation speed is advantageous in order to allow for appropriate amount of bone material to be removed while providing efficient cutting. When too many blades are used with a given blade shape, the flutes become very shallow and less bone material can be removed as a result. When an insufficient number of blades is used, the reamer head is not efficient in cutting bone tissue. In fact, the reamer head may bind or jam while cutting bone matter.

Figure 10:
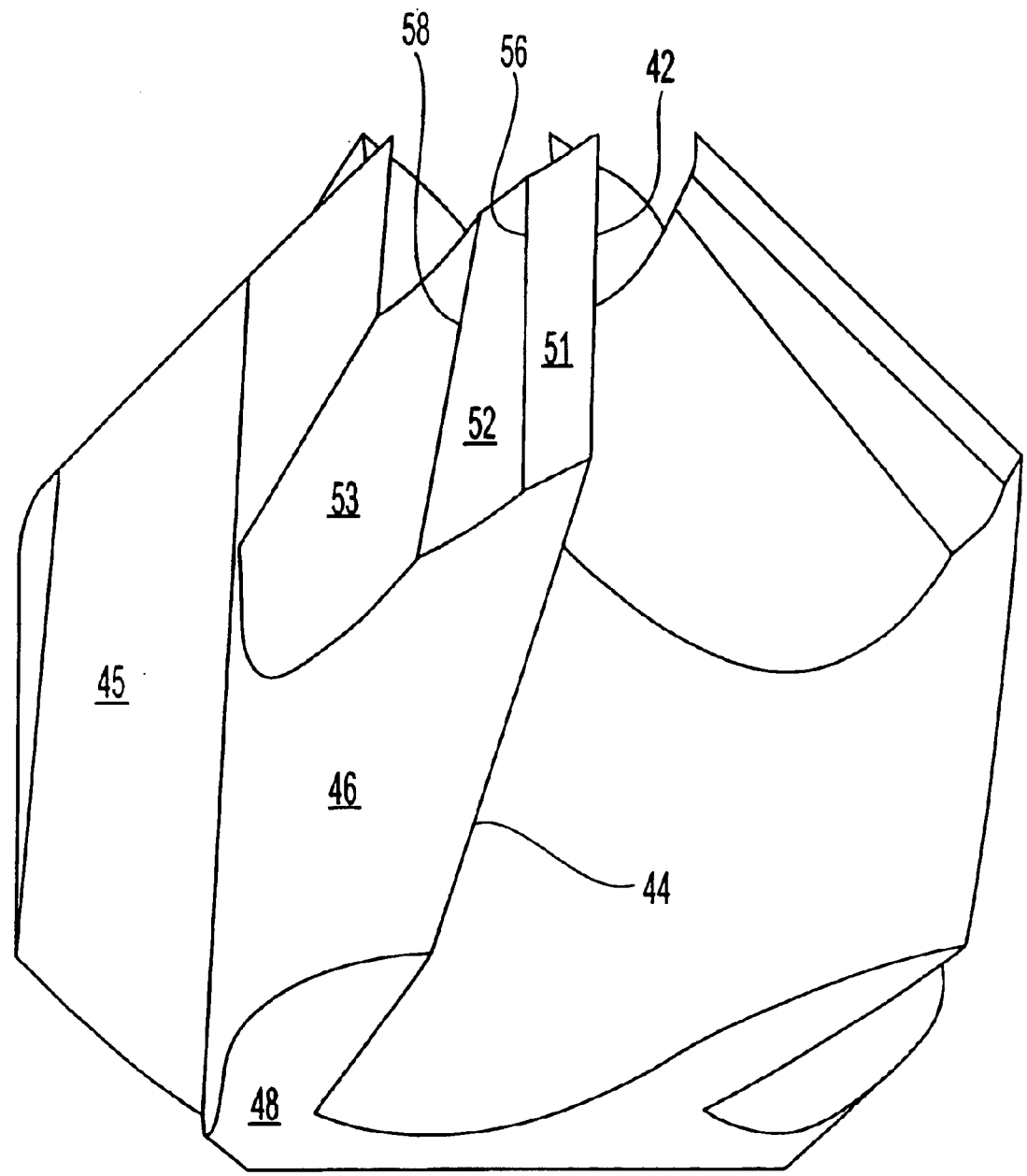
FIG. 10 is an enlarged view of a portion of FIG. 5.

As shown in FIG. 10, each blade 41 has a multiple surfaced angular distal end with a straight front cutting edge 42 joined to a helical side cutting edge 44. Front cutting edge 42 is defined by the intersection between an inner blade wall 45 and a planar first lip surface 51. The angle between inner blade wall 45 and first lip surface 51 is acute. A planar second lip surface 52 intersects first lip surface 51 at an obtuse angle to form a first lip edge 56. A planar third lip surface 53 intersects second lip surface 52 at an obtuse angle to form a trailing lip edge 58. Side cutting edge 44 is defined by the intersection between inner blade wall 45 and an outer blade surface 46 and is at a constant radial distance from the longitudinal axis and extends longitudinally in a helical fashion. Outer blade surface 46 whorls radially inward from side cutting edge 44 along an arc toward an inner blade wall of an adjacent blade. The space between such adjacent blades defines a flute 43 (shown in FIG. 9) which, during operation, functions to funnel the cut medullary canal material towards the proximal end of reamer head 20 for removal from the bone cavity through aspiration tube 13 under vacuum. Inner blade wall 45 and outer blade surface 46 extend longitudinally on cutting head 40 terminating at the proximal end in a shoulder surface 48. Shoulder surface 48 abuts tubular shank 25.

Figure 13:
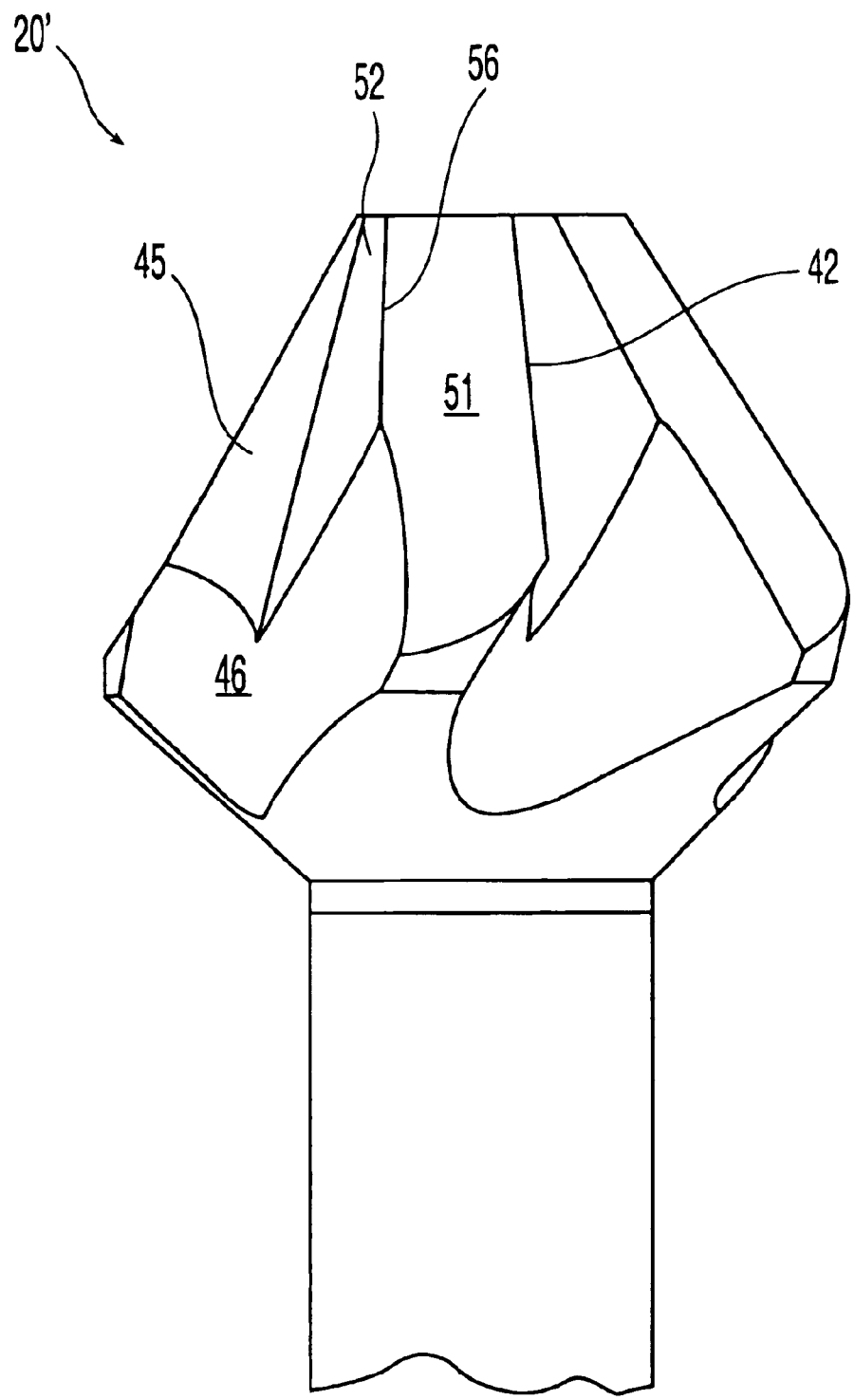
FIG. 13 is a top view of another embodiment of a reamer head according to the present invention.

FIG. 13 shows another embodiment of a reamer head 20' according to the present invention. Reamer head 20' does not have any side cutting edges, thereby substantially minimizing the risk of laterally reaming through the cortex of the bone. Each blade 41 has a multiple surfaced angular distal end with a straight front cutting edge 42. Front cutting edge 42 is defined by the intersection between an inner blade wall 45 and a planar first lip surface 51. The angle between inner blade wall 45 and first lip surface 51 is acute. A planar second lip surface 52 intersects first lip surface 51 at an obtuse angle to form a first lip edge 56. Outer blade surface 46 whorls radially inward along an arc toward an inner blade wall of an adjacent blade. The space between such adjacent blades defines a flute 43 which, during operation, functions to funnel the cut medullary canal material towards the proximal end of reamer head 20' for removal from the bone cavity through aspiration tube 13 under vacuum.

Figure 15:
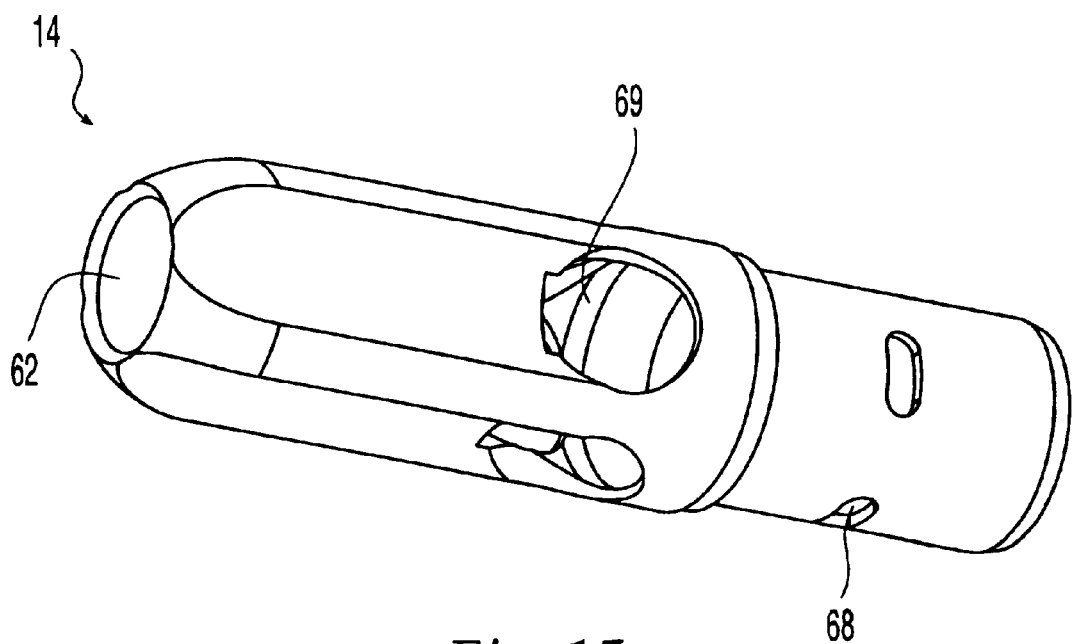
FIG. 15 is a perspective view of the reamer head retainer of FIG. 14.

FIGS. 14 and 15 shows reamer head retainer 14. Although reamer head retainer 14 can be of any shape with any number of ports 69, it is preferable that retainer 14 is substantially cylindrical in shape and has four ports 69 spaced at equal distance around the circumference of retainer 14. At the distal end of retainer 14 is opening 62 and bore 63 which are appropriately sized and shaped to receive tubular shank 25 and resilient arms 26 of reamer head 20. This can best be seen in FIG. 18. Located at the end of bore 63 is shoulder 64, which is used to engage resilient arms 26. The proximal end of reaming head retainer 14 is, preferably, smaller in diameter than its distal end. The proximal end of reaming head retainer 14 also has a plurality of openings 68 and bore 66 which, preferably, is larger in diameter than bore 63. Located between the proximal end and the distal end of retainer 14 is shoulder 67 which is used to engage retaining ring 11.

Figure 16:
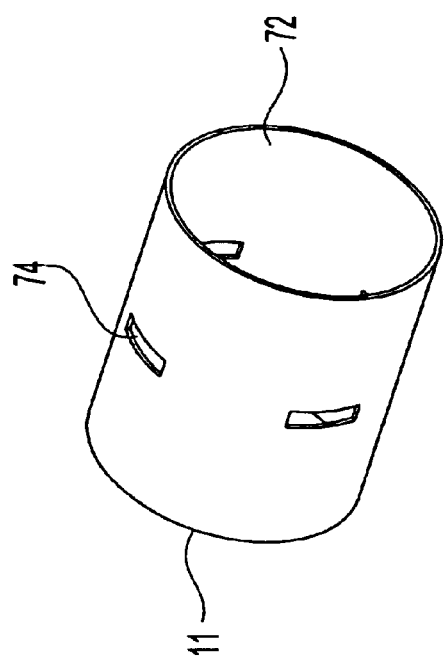
FIG. 16 is a perspective view of the retaining ring according to the present invention.

FIG. 16 shows retainer ring 11. Retainer ring 11 is, preferably, a tubular body having a bore 72 and a series of openings 74 disposed around its circumference.

Figure 17:
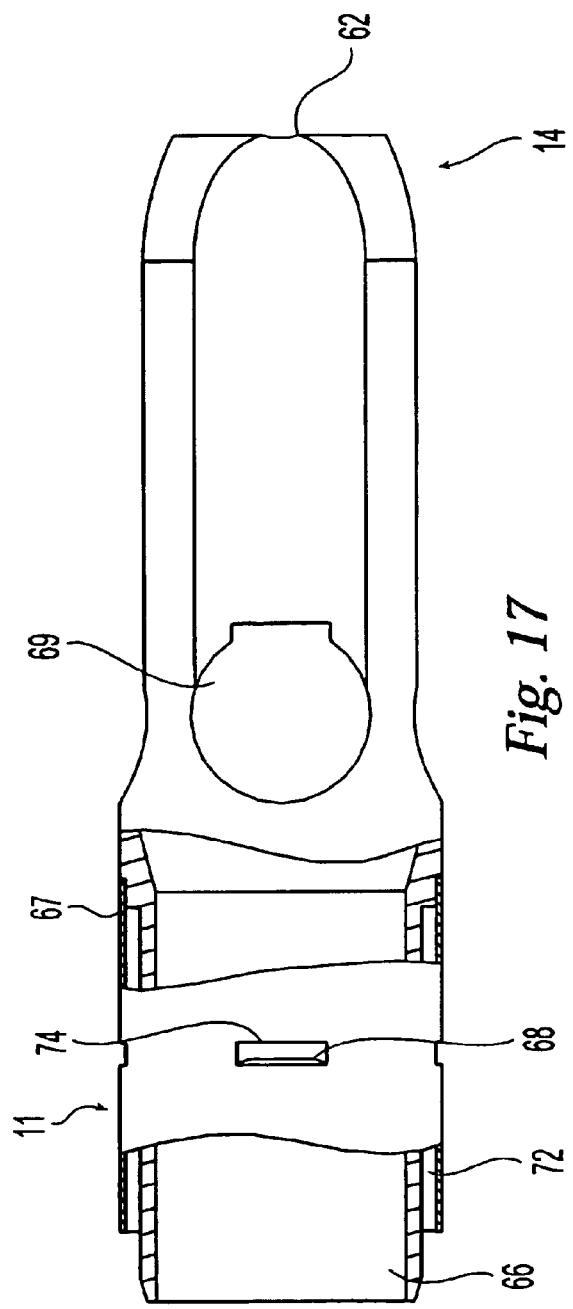
FIG. 17 is a partially fragmented cross-sectional and side view of the reamer head retainer of FIG. 14 engaged with the retaining ring of FIG. 16.
Figure 18:
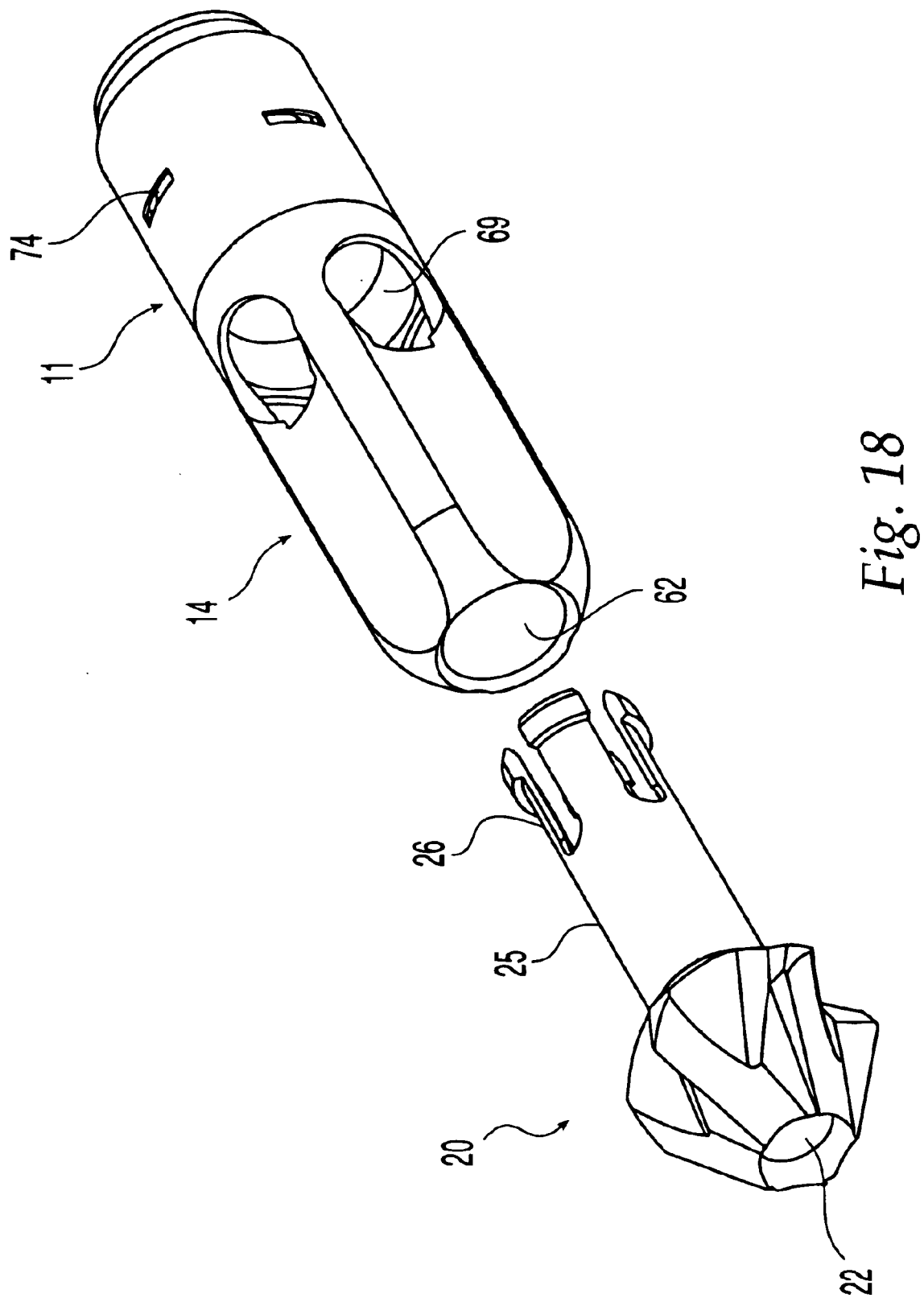
FIG. 18 is a perspective view of the reamer head of FIG. 13 aligned with the reamer head retainer of FIG. 14 and the retaining ring of FIG. 16.

FIGS. 17 and 18 show retainer ring 11 engaged to retainer 14 via shoulder 67. Although retainer ring 11 may be fastened to retainer 14 in any number of ways, it is preferable to fasten retainer ring 11 to retainer 14 via laser welding. When fastened openings 74 of retainer ring 11 are aligned with opening 68 of retainer 14. These opening are used to fixedly attach aspiration tube 13 to retaining ring 11 and retainer 14. As can best be seen in FIGS. 17 and 19, aspiration tube 13 fits in the space between retainer 14 and retaining ring 11. Once aspiration tube 13 is placed between retaining ring 11 and retainer 14, retaining ring 11, at openings 74, is staked through aspiration tube 13 and openings 68 in retainer 14 permanently fixing aspiration tube 13 to retainer ring 11 and retainer 14.

Figure 22:
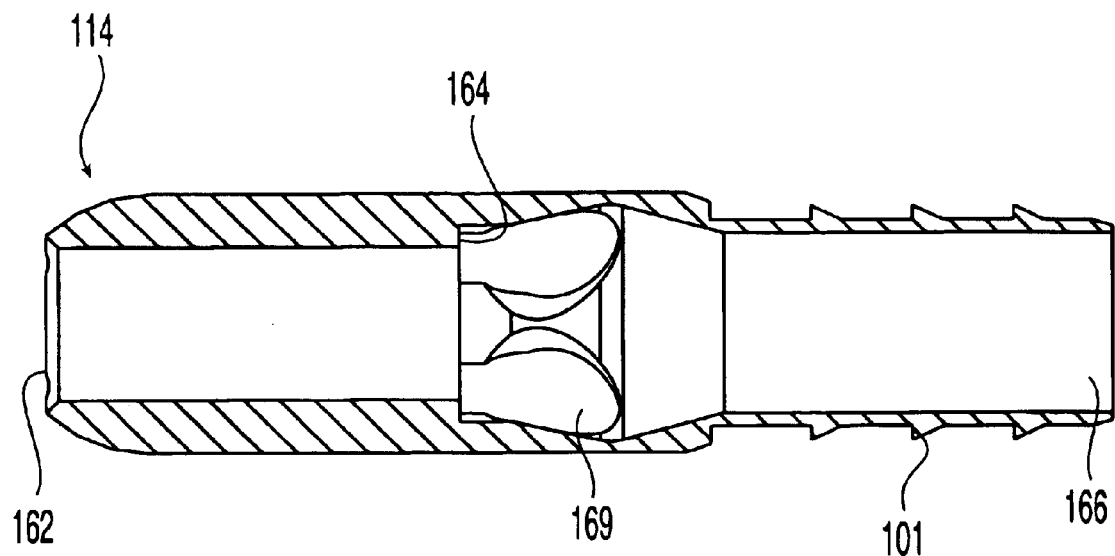
FIG. 22 is a cross-sectional view of another embodiment of the reamer head retainer according to the present invention.
Figure 23:
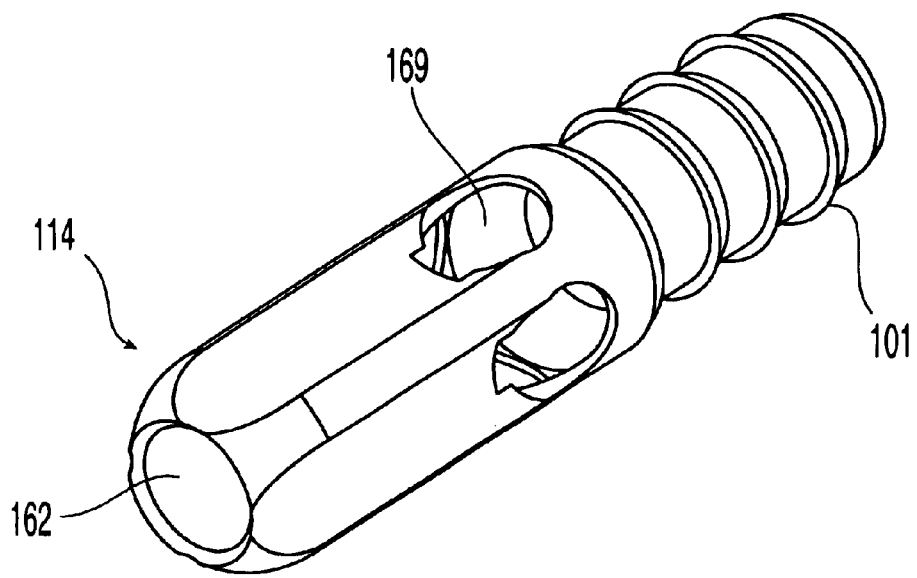
FIG. 23 is a perspective view of the reamer head retainer of FIG. 22.

FIGS. 22 and 23 show another embodiment of reamer head retainer 114. Although reamer head retainer 114 can be of any shape with any number of ports 169, it is preferable that retainer 114 is substantially cylindrical in shape and has four ports 169 spaced at equal distance around the circumference of retainer 114. At the distal end of retainer 114 is opening 162 and bore 163 which are appropriately sized and shaped to receive tubular shank 25 and resilient arms 26 of reamer head 20. Located at the end of bore 163 is shoulder 164, which is used to engage resilient arms 26. The proximal end of reaming head retainer 114 is, preferably, smaller in diameter than its distal end. The proximal end of reaming head retainer 114 also has a plurality of openings 168 and bore 166 which, preferably, is larger in diameter than bore 163. Located toward the proximal end of retainer 114 are protrusions 101 which are used to fixedly attach aspiration tube 13 to reamer head retainer 114. By having protrusion 101 fixedly attach aspiration tube 13 to reamer head retainer 114, retainer ring 11 is not needed.

Figure 19:
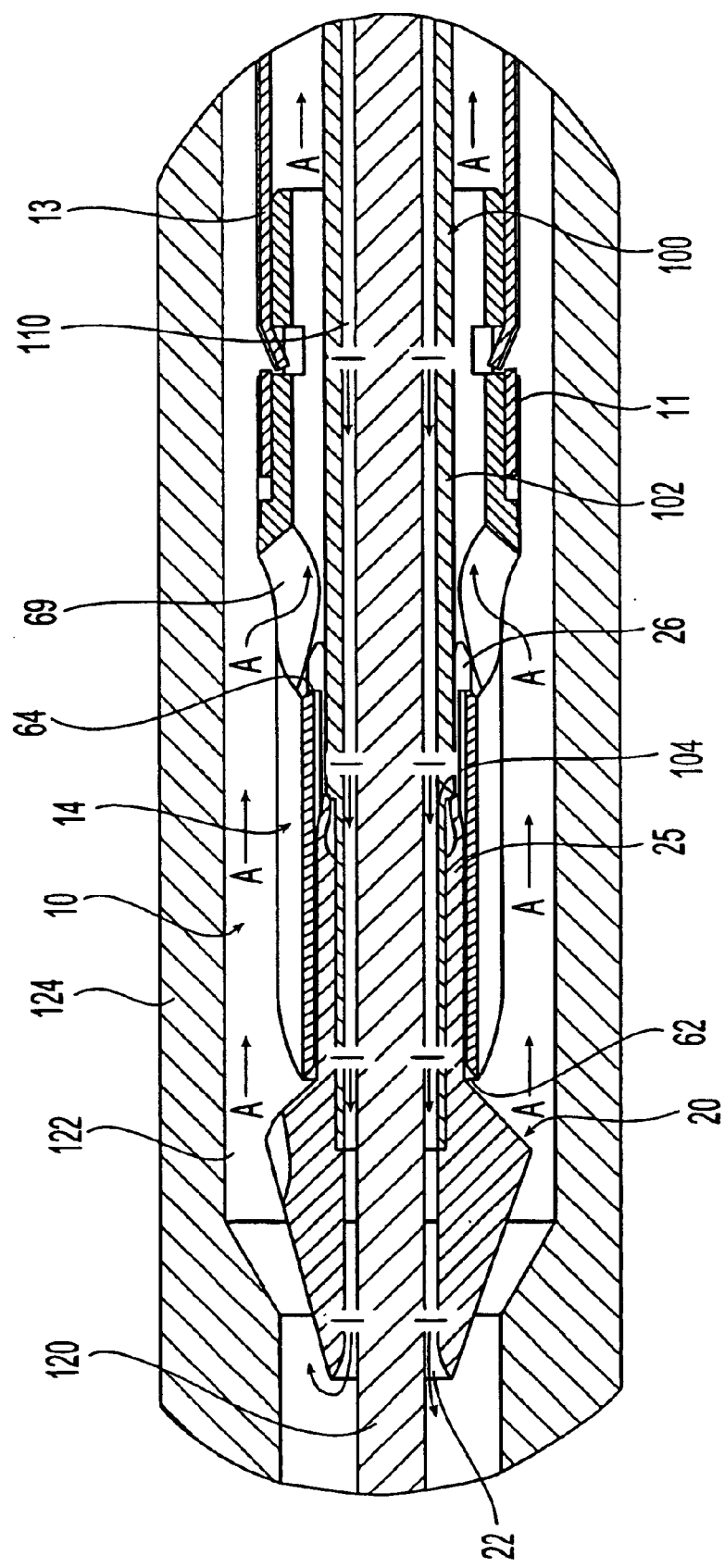
FIG. 19 is an enlarged and partially fragmented side and cross-sectional view of the reamer shown in FIGS. 1A and 1B.

The use of reamer 10, which can be during open surgical, percutaneous, or any other minimally invasive procedure, will now be described referring primarily to FIG. 19. After the bone to be reamed has been accessed, guide wire 120 is inserted into medullary canal 122 of bone 124. The insertion of guide wire 120 is typically done using fluoroscopy to ensure proper placement of guide wire 120. Reamer 10, with an appropriate cutter (such as reamer head 20 or 20') attached and coupled with drive shaft 100, is then placed over guide wire 120 so that guide wire 120 passes completely through aspiration tube 13 and provides a track which reamer 10 follows as it reams canal 122. Preferably, reamer 10 coupled with drive shaft 100, has been connected to a driving means prior to insertion into medullary canal 122. Thus, guide wire 120 actually passes through cannulation 110 of drive shaft 102 and cannulation 22 of reamer head 20. Furthermore, during use, the simultaneous rotation of drive shaft 102 and reamer head 20 over the guide wire 120 ensures patentcy of the cannulation while being introduced into the medullary canal.

While reaming medullary canal 122, irrigation and aspiration are applied simultaneously. The irrigation substantially cools reamer head 20, medullary canal 122, and bone 124. A preferable irrigation source, which delivers the irrigation fluid at a sufficient rate and pressure, is a normal saline bag suspended one meter above irrigation port 15. It should also be noted that, in addition to a saline bag, any biological compatible solution and delivery system can be used as the irrigation source. The irrigation fluid passes from the irrigation source into irrigation port 15 and enters irrigation chamber 35. The irrigation fluid, traveling along the path indicated by arrows I, flows through cannulation 110 in the space between the inner wall of cannulation and guide wire 120 and out of reamer head 20.

The aspiration alleviates intramedullary pressure and helps to remove emulsified material from reamer head 20. The removal of material not only improves reaming, but also provides for the possibility of harvesting the emulsified material for grafting purposes. Suction created by an aspiration source travels along the path indicated by arrows A. Specifically, the irrigation fluid helps to channel the emulsified material generated by reamer head 20 through flutes 43 and into the space between the outer wall of drive shaft 102 and the inner wall of aspiration tube 13 to transport the emulsified material from reamer head 20 through ports 69 in retainer 14, aspiration tube 13, and aspiration port 16 and into a suitable container.

A significant advantage of the system that includes reamer 10, detachable reamer head 20, and drive shaft assembly 100 is the ability to ream the medullary canal to the desired diameter in one pass, i.e. without the need to use multiple reaming heads of gradually increasing diameter until the desired reamed size is achieved. In this regard, supplying irrigation to reamer head 20 while simultaneously providing aspiration, and using a reamer head with an efficient front cutting geometry (and optionally a side cutting geometry) produces less pressure and heat than prior art reaming devices.

Figure 20:
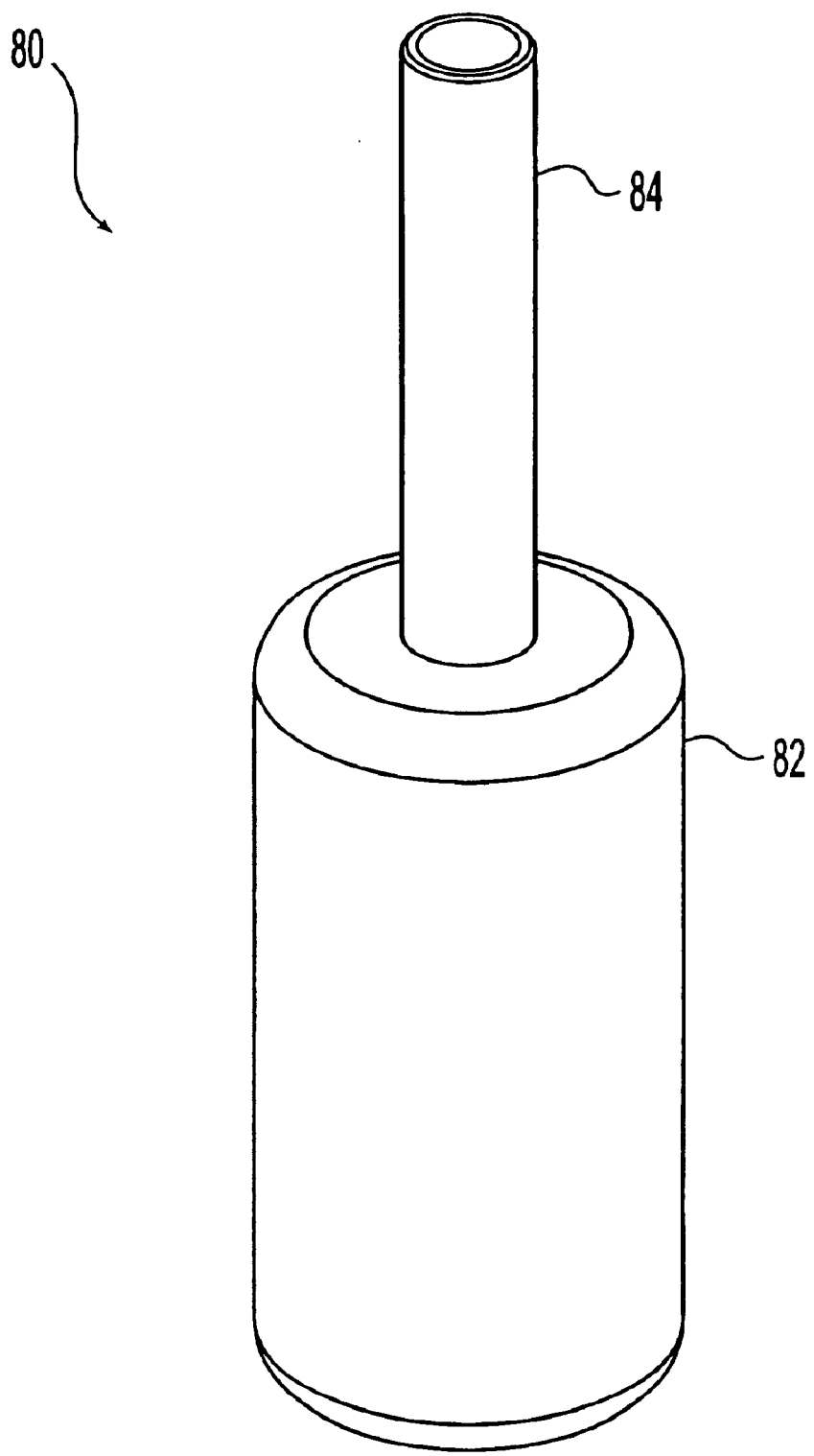
FIG. 20 is a perspective view of an embodiment of a reamer head removing device according to the present invention.
Figure 21:
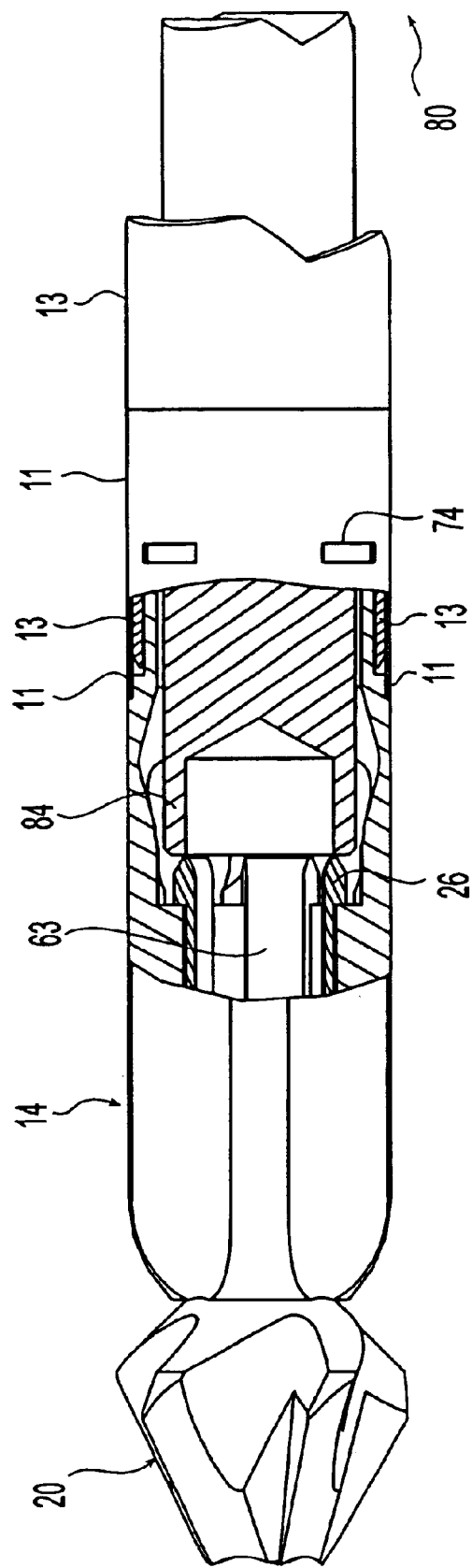
FIG. 21 is a partially fragmented side and cross-sectional view of the reamer shown in FIGS. 1A and 1B with the reamer head removal device of FIG. 20.

Once the reaming process is completed, depending on the amount of wear of the reaming head, the surgeon may want to detach the reaming head for future re-use. In order to detach the reamer head, drive shaft assembly 100 is first disengaged and removed from reamer head 20 and aspiration tube 13. Aspiration tube 13 is then cut at a location adjacent to the proximal end of the retaining ring and the remaining portion of aspiration tube 13 is thrown away. As can be seen in FIGS. 20 and 21, reamer head removing device 80, having a substantially cylindrical base 82 and engagement portion 84, is then inserted, proximally, through the remaining portion of aspiration tube 13, through retainer ring 11 and into retainer 14. As engagement portion 84 of removing device 80 is advanced toward the distal end of retainer 14, engagement portion 84 engages resilient arms 26 of reamer head 20 pushing them inwardly and unlocking them from shoulder 64 of retainer 14. Reamer head 20 can then be removed from retainer 14 and stored for future re-use.

While various descriptions of the present invention are described above, it should be understood that the various features can be used alone or in any combination. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A device for reaming a medullary canal of a bone comprising:
    a rotatable drive shaft having proximal and distal ends, the proximal end configured and adapted to connect to a drive element to rotate the drive shaft; and
    a reamer head coupled to the distal end of the drive shaft, to rotate the reamer head, said reamer head comprising:
        a tubular shank having a longitudinal axis and a plurality of resilient arms for engaging the distal end of the drive shaft; and
        a cutting head coupled with the shank and having a plurality of blades and flutes therebetween for cutting and reaming of bone;
    an aspiration tube for removing cut material generated by the reamer head, the aspiration tube having a manifold assembly at a proximal end and a lumen configured and dimensioned to receive the drive shaft; and
    a reamer head retainer having proximal and distal ends and configured and dimensioned at a proximal end to connect to a distal end of the aspiration tube and configured and dimensioned at a distal end to receive the reamer head,
    wherein the drive shaft and reamer head each has a cannulation, with the drive shaft cannulation aligning with the reamer head cannulation when the tubular shank and resilient arms are engaged with the drive shaft to form a center channel through the device.

2. The device of claim 1, wherein the manifold assembly has at least one port, the at least one port configured and adapted to communicate with an irrigation source, the at least one port is in fluid communication with the center channel.

3. The device of claim 1, wherein: the manifold assembly includes an irrigation port connectable to an irrigation source and an irrigation chamber in fluid connection with the irrigation port; and the drive shaft has an opening extending from an outer surface of the drive shaft to the drive shaft cannulation and located within the irrigation chamber.

4. The device of claim 1, wherein the manifold assembly includes an aspiration port connectable to a suction source.

5. The device of claim 1, wherein the reamer head retainer has a plurality of ports in fluid communication with the lumen of the aspiration tube.

6. The device of claim 1 wherein the reamer head retainer couples with the reamer head permitting the reamer head to rotate with respect to the retainer.

7. The device of claim 6, wherein the reamer head retainer has an internal shoulder for engaging the resilient arms of the reamer head.

8. The device of claim 1, further comprising: a reamer retaining ring coupled to the proximal end of the reamer head retainer and configured and dimensioned to fixedly attach the distal end of the aspiration tube to the proximal end of the reamer head retainer.

9. The device of claim 1, wherein the reamer head retainer has at least one protrusion located near the proximal end of the reamer head retainer for fixedly attaching the distal end of the aspiration tube to the proximal end of the reamer head retainer.

10. A device for reaming a medullary canal of a bone comprising:
    a rotatable drive shaft having proximal and distal ends, the proximal end configured and adapted to connect to a drive element to rotate the drive shaft; and
    a reamer head coupled to the distal end of the drive shaft, to rotate the reamer head, said reamer head comprising:
        a tubular shank having a longitudinal axis, the tubular shank configured and dimensioned for engaging the distal end of the drive shaft; and
        a cutting head coupled with the shank and having a plurality of blades and flutes therebetween for cutting and reaming of bone;
    an aspiration tube for removing cut material generated by the reamer head, the aspiration tube having a lumen configured and dimensioned to receive the drive shaft; and
    a reamer head retainer having proximal and distal ends and configured and dimensioned at a proximal end to connect to a distal end of the aspiration tube and configured and dimensioned at a distal end to receive the reamer head,
    wherein the drive shaft and reamer head each has a cannulation and wherein the reamer head retainer has a plurality of ports in fluid communication with the tlumen of the aspiration tube.

11. The device of claim 10, wherein the aspiration tube includes a manifold assembly at a proximal end.

12. The device of claim 11, wherein the manifold assembly has at least one port, the at least one port configured and adapted to communicate with an irrigation source.

13. The device of claim 11, wherein: the manifold assembly includes an irrigation port connectable to an irrigation source and an irrigation chamber in fluid connection with the irrigation port; and the drive shaft has an opening extending from an outer surface of the drive shaft to the drive shaft cannulation and located within the irrigation chamber.

14. The device of claim 11, wherein the manifold assembly includes an aspiration port connectable to a suction source.

15. The device of claim 10, wherein the reamer head retainer couples with the reamer head permitting the reamer head to rotate with respect to the retainer.

16. The device of claim 10, wherein the reamer head retainer has an internal shoulder for engaging a plurality of resilient arms formed on the reamer head.

17. The device of claim 10, further comprising: a reamer retaining ring coupled to the proximal end of the reamer head retainer and configured and dimensioned to fixedly attach the distal end of the aspiration tube to the proximal end of the reamer head retainer.

18. The device of claim 10, wherein the reamer head retainer has at least one protrusion located near the proximal end of the reamer head retainer for fixedly attaching the distal end of the aspiration tube to the proximal end of the reamer head retainer.

* * * * *

UNITED STATES PATENT AND TRADEMARK OFFICE
CERTIFICATE OF CORRECTION

PATENT NO. : 6,783,533 B2
DATED : August 31, 2004
INVENTOR(S) : Green et al.

It is certified that error appears in the above-identified patent and that said Letters Patent is hereby corrected as shown below:

Title page,
Item [73], Assignee, "Synthes AG Chur, Chur (CH)" should read -- Synthes (U.S.A.), Paoli, PA (US). --

Signed and Sealed this

Tenth Day of May, 2005

JON W. DUDAS
*Director of the United States Patent and Trademark Office*